United States Patent [19]

Fodor et al.

[11] Patent Number: 5,066,686

[45] Date of Patent: Nov. 19, 1991

[54] DEODORIZING ODOROUS POLYOLEFINS WITH LOW CONCENTRATIONS OF INORGANIC OXIDIZING AGENTS

[75] Inventors: Lawrence M. Fodor; Kenneth W. Willcox, both of Bartlesville, Okla.

[73] Assignee: Phillips Petroleum Company, Bartlesville, Okla.

[21] Appl. No.: 552,956

[22] Filed: Jul. 16, 1990

[51] Int. Cl.$^5$ .......................... A61L 2/16; C08K 3/38; C08K 3/22; C08K 3/16

[52] U.S. Cl. ................................... 523/102; 428/905; 428/907; 524/401; 524/405; 524/413; 524/423; 524/429

[58] Field of Search ................. 428/905, 907; 523/102, 523/124, 125; 525/337, 344, 387, 374, 377, 383; 524/405, 413, 429, 401, 423

[56] References Cited

U.S. PATENT DOCUMENTS

| | | | |
|---|---|---|---|
| 2,328,351 | 8/1947 | MacDonald | 523/102 |
| 2,455,910 | 12/1948 | Alderson | 525/387 |
| 2,507,143 | 5/1950 | Chaban | 524/405 |
| 2,801,446 | 8/1957 | Wolinski | 525/387 |
| 3,004,001 | 10/1961 | Robbins et al. | 260/45.95 |
| 3,012,020 | 12/1961 | Kirk et al. | 525/387 |
| 3,020,258 | 2/1962 | Robbins | 260/45.9 |
| 3,028,363 | 4/1962 | Robbins et al. | 260/45.85 |
| 3,162,608 | 12/1964 | Mattano | 260/2.1 |
| 3,171,824 | 3/1965 | Young | 260/27 |
| 3,257,366 | 6/1966 | Monroe et al. | 524/401 |
| 3,271,349 | 9/1966 | Levey et al. | 523/102 |
| 3,795,654 | 3/1974 | Kirkpatrick | 523/124 |
| 4,104,424 | 8/1978 | Steinbrecher et al. | 524/429 |
| 4,185,008 | 1/1980 | Caspari et al. | 524/429 |
| 4,678,684 | 7/1987 | Sand | 523/102 |
| 4,929,717 | 5/1990 | Chmelir | 525/377 |

FOREIGN PATENT DOCUMENTS 58-112929 7/1983 Japan.
1195099 6/1970 United Kingdom.

OTHER PUBLICATIONS

T. J. Hermans, "Meet Stabilization of Polypropylene", *Developments in Polymer Stabilization*-1, by Gerald Scott, pp. 39-97 (1981).

*Primary Examiner*—Veronica P. Hoke
*Attorney, Agent, or Firm*—Carl D. Corvin

[57] ABSTRACT

This invention relates to deodorizing odorous polyolefins. This is accomplished by mixing the odorous polyolefin with low concentration levels of an inorganic oxidant. Optionally, a fragrance is mixed with the odorous polyolefin mixture. Additionally, if desired, heat can be applied to the mixture.

16 Claims, No Drawings

DEODORIZING ODOROUS POLYOLEFINS WITH LOW CONCENTRATIONS OF INORGANIC OXIDIZING AGENTS

BACKGROUND OF THE INVENTION

This invention relates to a process for deodorizing odorous polyolefins.

Various methods are known to produce polyolefins. These polyolefin type compounds have been used in a wide variety of applications. For example, polyolefins are fabricated into molded articles such as pipes, films, and fibers. However, one persistent problem that has limited the development of polyolefin applications has been the generation of odorous compounds during the production of the polyolefin. These odorous compounds are then incorporated into the polyolefin material. After incorporation, these odorous compounds interfere with the utilization of the polyolefin material in applications where such odors would be undesirable. An example of this occurs when a polyolefin resin is used to fabricate a container for a liquid or a solid which is meant for human consumption, and that polyolefin container has a distasteful olfactory impact upon the consumer of the product.

Considering the subjectiveness of determining an odor's quality it is best if there are not any odorous compounds in the polyolefin material at all. However, it is hard, if not impossible sometimes, to determine exactly which compound, in a group of compounds, is odorous. Given the difficulties in determining which compounds are odorous, and in eliminating those odorous compounds from the polyolefin material, it is reasonable to eliminate the suspected odorous properties of the various suspected odorous compounds in order to lessen their net impact upon the final application of the polyolefin material.

SUMMARY OF THE INVENTION

It is an object of this invention to provide a process to deodorize odorous polyolefins.

It is another object of this invention to provide a process to lower the odor intensity of odorous polyolefins.

It is yet another object of this invention to neutralize the odor quality of odorous polyolefins.

In accordance with this invention, an inorganic oxidizer is mixed with the odorous polyolefin.

DETAILED DESCRIPTION OF THE INVENTION

Polyolefins

This invention is broadly applicable to polyolefins. Examples of polymerizable olefins which can be used to produce these polyolefins include, but are not limited to, those olefins which contain from 2 to 30 carbon atoms per molecule. However, more preferably, these olefins contain from 2 to 20 carbon atoms per molecule. The molecular structure of these polymerizable olefins can also be either linear or branched. Additionally, these polymerizable olefins can be polymerized alone to give a homopolymer or they can be polymerized with another monomer to give a copolymer. Individual molecular examples of polymerizable olefins include, but are not limited to, ethylene, propylene, butene, pentene, hexene, heptene, octene, 3-methyl-1-butene, 3-methyl-1pentene, 4-methyl-1-pentene, 4-methyl-1-hexene, 3-ethyl-1-hexene, 3,3-dimethyl-1-butene, 4,4-dimethyl-1-hexene, decene, dodecene, tetradecene, hexadecene, conjugated and/or non-conjugated diolefins such as 1,3-butadiene, isoprene, piperylene, 2,3-dimethyl-1,3-butadiene, 1,4-pentadiene, 1,7-hexadiene.

Inorganic Oxidizing Agents

In general, the term "inorganic oxidizing agent" refers to those non-carbon containing compounds which tend to be electron acceptors in oxidation-reduction type reactions. The term includes, but it not limited to, such classes of chemicals as inorganic peroxides, chlorates, perchlorates, nitrates, and permanganates. These types of oxidizing agents can react vigorously at ambient temperatures when stored near or in contact with reducible materials such as formaldehyde and other organic compounds.

Individual examples of the types of inorganic oxidizing agents that can be utilized are:

1. Permanganates: typical examples include potassium permanganate and sodium permanganate. Although permanganates can be used as an inorganic oxidizing agent, they tend as a group to impart an unacceptable color to the polyolefin. Thus they are not as useful as the other classes;

2. Nitrates: typical examples of nitrates include calcium nitrate and potassium nitrate;

3. Perchlorates: typical examples include ammonium perchlorate, potassium perchlorate and sodium perchlorate. Although there are many perchlorates in all of the groups of the periodic table, perchlorates of group IA and group IIA are preferred over the other perchlorates;

4. Chlorates: typical examples include sodium chlorate and potassium chlorate;

5. Peroxides: typical examples include hydrogen peroxide, sodium peroxide, sodium peroxyborate.

Other examples include such compounds as sodium hypochlorite and potassium persulfate. Of these types of compounds hydrogen peroxide is most preferred due to its availability, reactivity and lack of undesireable residuals left in the polymer after treatment.

Hydrogen Peroxide

The hydrogen peroxide used in this invention can be of any concentration. The required hydrogen peroxide can be obtained in concentrations ranging from about 3 to about 98 percent by weight based on the total weight of peroxide and water. However, the preferred concentration of hydrogen peroxide to use is from about 3 to about 70 percent by weight. Even more preferably a concentration of hydrogen peroxide is from about 3 to about 30 percent by weight. Concentrations above about 70 weight percent promote organic oxidation and require special handling procedures. Concentrations below about 3 weight percent are expensive to stabilize and transport thus increasing processing costs.

Amount of Inorganic Oxidizing Agent to Use

The amount of inorganic oxidizing agent to mix with the odorous polyolefin is preferably from about 0.0001 to about 0.1 weight percent based on the weight of the polyolefin. However more preferably, the inorganic oxidizing agent is from about 0.0005 to about 0.05 weight percent, and most preferably from about 0.001 to about 0.02 weight percent, where all the weight percents are based on the weight of the polyolefin.

If too much inorganic oxidizing agent is added this will promote undesirable side effects such as cross-linking and vis-breaking in the polyolefin material. If too little inorganic oxidizing agent is added the odor intensity and odor quality of the odorous polyolefin might be unaffected. Preferably, the amount added lowers the odor intensity and neutralizes the odor quality of the odorous polyolefin.

It should be noted that inorganic oxidizing agents can present a serious safety hazard. Great care should be taken when handling these compounds especially when these compounds are in contact with organic materials.

Fragrance

Optionally, a fragrance may be mixed with the inorganic oxidizing agent and odorous polyolefin. The type of fragrance to add depends on the particular properties of the fragrance and the end use of the polyolefin. Some types of fragrances to add are, for example, lemon oil, lime oil, mandarin oil, verbena, and lemon grass oil.

The amount of fragrance to mix with the odorous polyolefin is preferably from about 0.0025 to about 0.1 weight percent based on the weight of the polyolefin. However, more preferably the amount of fragrance to add is from about 0.005 to about 0.075 weight percent and most preferably, it is from about 0.0075 to about 0.05 weight percent, where all the weight percents are based on the weight of the polyolefin.

If too much fragrance is added the fragrance will adversely odorize the odorous polyolefin resulting in undesirable olfactory impact upon the end user of the polyolefin. If too little fragrance is added the odor intensity and odor quality will not be beneficially changed. Preferably, the amount added lowers the odor intensity and neutralizes the odor quality of the odorous polyolefin.

Heat

Optionally, heat may be applied to the polyolefin mixture that contains the inorganic oxidizing agent and optionally a fragrance. The heat can be applied by any known method in the art. The amount of heat to be applied depends on the type of polyolefin that is to be deodorized. Generally, the temperatures at which the polyolefin is deodorized is below the melting point of that polyolefin. For example, polypropylene should be deodorized below its melting point of about 160°C. If the temperature at which the polyolefin is deodorized is too high this could produce undesirable side effects such as structural degradation. If the temperature at which the polyolefin is deodorized is too low the process will proceed too slowly to be economically useful.

Reaction Conditions

The inorganic oxidizing agent can be mixed with the polyolefin at any time after its formation and removal from the reactor. However, this process should be done before the polyolefin is finally processed. For example, this process could be accomplished after the polyolefin is formed, but before the polyolefin is passed through an extruder. As a further example, the polyolefin after its removal from the reactor, could be placed in a mixer where an inorganic oxidizer is added. Optionally, at this time, a fragrance can also be added. The resulting mixture could then, if desired, be passed through a Double Agitator Heat Treater where frictional heat could be applied. Additionally, as another example, the polyolefin after its removal from the reactor, could be passed through a purge conveyor where an inorganic oxidizer is mixed with the polyolefin. Additionally, a fragrance can be added, as well as heat applied to the polyolefin mixture as it passes through the purge conveyor. It should be noted that it is known in the art to protect a polyolefin by the addition of antioxidants to the polyolefin material. Therefore, this invention would seem to run in opposition to accepted practice. While not wanting to be bound by theory, it is believed that the addition of the inorganic oxidizing agent decreases the odor intensity and neutralizes the odor quality of the polyolefin by preferentially attacking the odorous compounds while essentially leaving the antioxidant protected polyolefin unharmed.

This process can be done under pressure with an upper pressure limit of about 10,000 psi. However, near atmospheric pressure is preferred for ease of processing and for safety reasons.

The polyolefin can be left in contact with the inorganic oxidizer, for about five seconds to about five hours. However, more preferably, the polyolefin is left in contact for about one minute to about 3 hours. If the polyolefin is allowed contact with the inorganic oxidizer for too long, undesirable side effects may occur. For example, the process might generate free radicals in unwanted amounts causing damage to the polyolefin. If the polyolefin is not allowed sufficient contact time with the process then the polyolefin will not be sufficiently deodorized. Additionally, if heat is applied to the polyolefin for too long of a time structural degradation could occur.

This process can be accomplished under different types of media. For example, the process can be carried out in an inert atmosphere, a nitrogen atmosphere, or any normal atmosphere. However, the atmosphere chosen should not be highly reactive with the inorganic oxidizer in order to lessen the risk of a safety hazard.

As a further help in understanding the present invention and its advantages the following example is provided.

EXAMPLE

A Dynamic Dilution Binary Scale Olfactometer (DDBSO) was used to reference the odor intensity of the samples. This referencing device is similar to that described in ASTM E544-75 (reapproved 1988). This ASTM is a standard for referencing suprathreshold odor intensity. However, this standard only references odor intensity and not odor quality.

The DDBSO provided reference data by continuously and simultaneously preparing an air/odor vapor mixture at eight different concentration levels. These concentration levels followed a geometric progression with each succeeding level being a factor of 2 greater than its preceding level. For example, the concentration level at 4 was about twice as much as the concentration level at 3, yet level 4 had half as much as the concentration level at 5. This measure of the odor intensity was a measure of how strong the odor was perceived by the odor panelists while they ignored the odor quality. The odor panelists responded on a scale of 1 to 8 where 1 represented the lowest odor intensity and 8 represented the strongest odor intensity.

The odor quality (also referred to in the art as the hedonic tone) was a measure of how pleasant or how revolting a particular odor was perceived. This odor quality was measured on a $-3$ to a $+3$ scale where $-3$ represented a revolting odor and $+3$ represented a pleasant odor. The 0 point on this scale represented a neutral odor quality. For commercial reasons a neutral odor quality is usually desirable for a polyolefin product.

The reactants used in this example were hydrogen peroxide, Naarden lemon oil, IFF "Golden Forest", and polypropylene. The hydrogen peroxide used was an aqueous 30 weight percent solution which is commercially available. The Naarden lemon oil is commercially available on the market. IFF "Golden Forest" is a fragrance from the International Fragrance and Flavor Company. The polypropylene was in the form of powder. This powder was made by methods known in the art. After treatment, this polypropylene powder was then formed into pellets or into blow molded bottles to be odor sampled. The device used to apply heat to the process was a Double Agitator Heat Treater also known in the art as a Wedco polisher. This device imparts heat to the odorous polyolefin mixture by frictional means. The device employs no external heat source and no heat transfer media. Essentially, all power delivered from the drive motor to the agitator is transferred directly to the material thus providing frictional heating to the material. The Double Agitator Heat Treater was operated at a temperature of 115° C.

Preparation of the Samples

The untreated samples (runs 01 and 11) were prepared by taking untreated polypropylene powder and forming it into pellets (run 01) or into a blow molded bottle (run 11).

Runs 02 through 10 were prepared by adding the listed embodiments and then forming the polypropylene into pellets. For example in run 04, 0.01 weight percent of lemon oil and 0.01 weight percent of hydrogen peroxide were mixed with untreated polyproylene powder. Next this mixture was passed through the Double Agitator Heat Treater where the heat was added. Finally, the treated polypropylene was pelleted for sampling.

Runs 12 through 21 were prepared the same way runs 02 through 10 were prepared except that they were further formed into blow molded bottles.

Column Explanation

Column A represents the type of sample used. In this column "Pellet" represents a polypropylene pellet sample, while a "Bottle" represents a polypropylene blow-molded bottle sample. These two types of samples were selected because:

1) the pellet samples give a good indication of the odor of the polypropylene as it leaves the plant site; and 2) the blow-molded bottles give a reasonable indication of the odor of the polypropylene after being shaped into its end use form. However, this data would be greatly affected by the type of shaping method used by the end product shaper. The reason is that these shaping methods can impart additional odors to the polypropylene.

Additionally, the blow-mold bottle samples were heated for two hours at 60° C. then cooled to room temperature before sampling.

Column B indicates how much 30% aqueous hydrogen peroxide was added. This figure is the weight percent of hydrogen peroxide where the weight percent of the hydrogen peroxide is based on the weight of the polypropylene.

Column C indicates whether a Wedco polisher was used on the sample. A "YES" indicates that the sample was run through the Wedco polisher and an "NO" indicates that the sample was not run through the Wedco polisher.

Column D indicates how much Naarden lemon oil was added. This figure is the weight percent of lemon oil where the weight percent of the lemon oil is based on the weight of the polypropylene.

Column E represents how much IFF "Golden Forest" was added. This figure is the weight percent of IFF "Golden Forest" where the weight percent of IFF "Golden Forest" is based on the weight of the polypropylene. IFF "Golden Forest" is based on the weight of the polypropylene. IFF "Golden Forest" stands for the International Fragrance and Flavors Company's fragrance called "Golden Forest."

Column F represents the average of the odor panelists' reaction to the odor intensity. This was measured on a scale of 1-8 where 1 represented the lowest intensity and 8 represented the strongest intensity. Additionally, each increment of one represents a factor of two increase or decrease in the odor intensity. For example, in run number 01 the odor intensity was 5.3 whereas, in run number 04 the odor intensity was 3.5, this change in the odor intensity of 1.8 units (5.3 to 3.5) represents a nearly four fold decrease in the odor intensity of the sample.

Column G represents the average of the odor panelists' reactions to the odor quality. This was measured on a scale of $-3$ to $+3$, where $-3$ represented a revolting odor, zero represented a neutral odor, and $+3$ represented a pleasant odor.

Column H represents the range of responses given by the odor panelists when they sampled the odorous polypropylene. This was measured using the same scale as in column G. For example, in run number 01 several odor panelists thought that the untreated polypropylene pellets had an unpleasant odor, while others thought that the untreated polypropylene had a neutral odor. Whereas, in run number 04 the odor panelists thought that the treated polypropylene had either a neutral odor or a pleasant odor.

Column I represents the net change in the odor quality of the treated polypropylene sample when compared to the untreated polypropylene sample. In other words, each odor panelists' perception of the treated polypropylene was compared to their perception of the untreated polypropylene. The change in these perceptions is the data that is recorded in column I. For example, in run number 21 some odor panelists definitely thought that the addition of Naarden lemon oil worsened the odor while others thought that this addition improved the odor when compared to the untreated blow molded bottle sample. In contrast, in run number 04 the odor panelists thought that the added constituents either did not change the odor quality or thought the odor was greatly improved when compared to the untreated pellet sample. Additionally, each treated sample was only compared with the similar type untreated sample. In other words, samples of treated polypropylene pellets (runs 02 through 10) were compared with the untreated polypropylene pellets (run 01), whereas samples of treated polypropylene blow molded bottles (runs 12 through 21) were compared with the untreated polypropylene blow molded bottle (run 11).

| RUN NUMBER | A TYPE OF SAMPLE | B HYDROGEN PEROXIDE | C HEAT | D LEMON OIL | E IFFGF | F ODOR INTENSITY | G VALUE | H ODOR QUALITY RANGE | I CHANGE |
|---|---|---|---|---|---|---|---|---|---|
| 01 | PELLET | 0.00 | NO  | 0.00 | 0.0000 | 5.3 | −1.3 | −2 → 0  | N/A |
| 02 | PELLET | 0.01 | NO  | 0.00 | 0.0000 | 5.3 | −0.5 | −2 → +1 | 0 → +2 |
| 03 | PELLET | 0.01 | YES | 0.00 | 0.0000 | 4.0 | 0    | −1 → +1 | 0 → +3 |
| 04 | PELLET | 0.01 | YES | 0.01 | 0.0000 | 3.5 | +0.5 | 0 → +2  | 0 → +4 |
| 05 | PELLET | 0.01 | YES | 0.00 | 0.0025 | 5.3 | +1   | 0       | +1 → +3 |
| 06 | PELLET | 0.01 | NO  | 0.01 | 0.0000 | 5.0 | 0    | −1 → +1 | 0 → +3 |
| 07 | PELLET | 0.01 | NO  | 0.00 | 0.0025 | 5.3 | +0.3 | −1 → +1 | 0 → +3 |
| 08 | PELLET | 0.00 | YES | 0.00 | 0.0000 | 4.3 | −1   | −3 → 0  | −1 → +1 |
| 09 | PELLET | 0.00 | YES | 0.01 | 0.0000 | 4.5 | +1.3 | −1 → +3 | 0 → +4 |
| 10 | PELLET | 0.00 | YES | 0.00 | 0.0025 | 4.5 | +0.8 | −1 → +2 | −1 → +4 |
| 11 | BOTTLE | 0.00 | NO  | 0.00 | 0.0000 | 5.3 | −1   | −2 → 0  | N/A |
| 12 | BOTTLE | 0.01 | NO  | 0.00 | 0.0000 | 5.3 | −0.8 | −2 → 0  | −1 → +1 |
| 13 | BOTTLE | 0.01 | YES | 0.00 | 0.0000 | 4.3 | −0.5 | −1 → 0  | −1 → +2 |
| 14 | BOTTLE | 0.01 | YES | 0.01 | 0.0000 | 4.5 | −0.8 | −2 → +1 | −1 → +2 |
| 15 | BOTTLE | 0.01 | YES | 0.00 | 0.0025 | 4.3 | −1   | −2 → 0  | −1 → +1 |
| 16 | BOTTLE | 0.01 | NO  | 0.01 | 0.0000 | 4.5 | −0.5 | −1 → +1 | −1 → +2 |
| 17 | BOTTLE | 0.01 | NO  | 0.00 | 0.0025 | 5.8 | −1   | −2 → +1 | −1 → +2 |
| 18 | BOTTLE | 0.00 | YES | 0.00 | 0.0000 | 6.0 | −1.8 | −3 → −1 | −3 → 0 |
| 19 | BOTTLE | 0.00 | YES | 0.01 | 0.0000 | 4.0 | −0.3 | −1 → +1 | −1 → +2 |
| 20 | BOTTLE | 0.00 | YES | 0.00 | 0.0025 | 4.3 | −0.5 | −1 → +1 | −1 → +2 |
| 21 | BOTTLE | 0.00 | NO  | 0.01 | 0.0000 | 3.8 | −0.8 | −3 → +1 | −2 → +2 |

From the above data it is apparent that the odor intensity was improved the best by run number 04. This run which included the optional constituents and showed an odor intensity improvement of 34% (5.3 to 3.5) on the binary geometric progression odor intensity scale. Additionally, it is apparent that the odor quality, as reported by the odor panelists, was improved from −1.3 to 0.5 on the odor quality scale. Furthermore, run 04 showed that the run had one of the greatest beneficial impacts on the odorous polypropylene with the odor panelists reporting that either they did not change their perception of the odorous polypropylene (a score of 0) or that their perception was changed greatly (a score of +4). And lastly, run 04 was the only run the odor panelists reported that the odor quality was either neutral or pleasant in their perception.

Additionally, it should be noted that all of the runs using the peroxide showed improvement due to the peroxide alone. For example, a comparison of runs 01 and 02 shows an improvement in the odor quality. A comparison of runs 03 and 08 shows that the addition of the peroxide to the heat treated sample improved the odor intensity and the odor quality. Similarly in runs 11 and 12 an improvement in the odor quality was reported. Furthermore, a comparison of 13 and 18 showed an improvement in both the odor quality and odor intensity.

While this invention has been described in detail for the purpose of illustration it is not to be construed as limited thereby, but is intended to cover all changes and modifications within the spirit and scope thereof.

That which is claimed is:

1. A process for deodorizing odorous aliphatic polyolefins which comprises:
    (a) contacting about 0.0001 weight percent to about 0.1 weight percent of inorganic oxidizing agent selected from the group consisting of ammonium perchlorate, potassium perchlorate, sodium perchlorate, sodium chlorate, potassium chlorate, sodium peroxide, sodium peroxyborate, hydrogen peroxide, and mixtures thereof, where the weight percent of inorganic oxidizing agent is based upon the weight of the aliphatic polyolefin; with
    (b) said odorous aliphatic polyolefin;
to reduce the odor intensity and neutralize the odor quality of said aliphatic polyolefin.

2. A process according to claim 1 wherein said inorganic oxidizing agent is hydrogen peroxide.

3. A process according to claim 1 further comprising contacting about 0.0025 weight percent to about 0.1 weight percent of fragrance where the weight percent of fragrance is based upon the weight of the aliphatic polyolefin; with said inorganic oxidizing agent and said odorous aliphatic polyolefin to reduce the odor intensity and neutralize the odor quality of the polyolefin.

4. A process according to claim 3 wherein the fragrance is selected from the group consisting of lemon oil, lime oil, mandarin oil, verbena, lemon-grass oil, and mixtures thereof.

5. A process according to claim 3 wherein the fragrance is lemon oil.

6. A process according to claim 1 further comprising heating the polyolefin and inorganic oxidizing agent mixture to a temperature sufficient to reduce the odor intensity and neutralize the odor quality of the polyolefin.

7. A process according to claim 6 where the temperature is below the melting point of the polyolefin.

8. A process according to claim 3 further comprising heating the polyolefin, inorganic oxidizing agent, and fragrance mixture to a temperature sufficient to reduce the odor intensity and neutralize the odor quality of the polyolefin.

9. A process according to claim 8 where the temperature is below the melting point of the polyolefin.

10. A process for deodorizing odorous polypropylene which comprises:
    (a) mixing with the odorous polypropylene, about 0.0001 weight percent to about 0.1 weight percent of hydrogen peroxide, where the weight percent of hydrogen peroxide is based upon the weight of the polypropylene;
    (b) mixing with the odorous polypropylene, about 0.0025 weight percent to about 0.1 weight percent of lemon oil where the weight percent of lemon oil is based upon the weight of the polypropylene; and
    (c) heating the odorous polypropylene, hydrogen peroxide, and lemon oil mixture to a temperature below the melting point of the polypropylene to reduce the odor intensity and neutralize the odor quality of the odorous polypropylene.

11. A process for deodorizing aliphatic polyolefins which comprises:
(a) forming a powdered aliphatic polyolefin product;
(b) contacting said powdered aliphatic polyolefin product with an antioxident to form an antioxident protected polyolefin;
(c) contacting said antioxident protected polyolefin with about 0.0001 to about 0.1 weight percent of inorganic oxidizing agent where the weight percent of inorganic oxidizing agent is based upon the weight of said powdered aliphatic polyolefin product; and
(d) extruding the product of step (c).

12. A process according to claim 11 wherein said contacting step (c) occurs for about 5 seconds to about 5 hours.

13. A process according to claim 11 wherein step (c) further comprising heating at a temperature below the melting point of said powdered aliphatic polyolefin product.

14. A process according to claim 11 wherein step (c) further comprises contacting with about 0.0025 to about 0.1 weight percent of fragrance wherein the weight percent of fragrance is based on the weight of said powdered aliphatic polyolefin product.

15. A process according to claim 14 wherein the fragrance is selected from the group consisting of lemon oil, lime oil, mandarin oil, verbena, lemon-grass oil, and mixtures thereof.

16. A process according to claim 14 wherein the fragrance is lemon oil.

* * * * *